United States Patent [19]

Fridge

[11] Patent Number: 4,648,053

[45] Date of Patent: Mar. 3, 1987

[54] HIGH SPEED OPTICAL INSPECTION SYSTEM

[75] Inventor: David A. Fridge, Glendale, Calif.

[73] Assignee: Kollmorgen Technologies, Corp., Melville, N.Y.

[21] Appl. No.: 666,501

[22] Filed: Oct. 30, 1984

[51] Int. Cl.$^4$ .................... G01B 11/24; H04N 7/18
[52] U.S. Cl. .................... 364/551; 358/101; 356/390
[58] Field of Search .............. 364/551; 358/101, 106, 358/107; 356/390, 237

[56] References Cited

U.S. PATENT DOCUMENTS

| | | | |
|---|---|---|---|
| 3,887,762 | 6/1975 | Uno et al. | 358/101 |
| 4,185,298 | 1/1980 | Billet et al. | 356/390 |
| 4,295,198 | 10/1981 | Copeland et al. | 358/101 |
| 4,379,308 | 4/1983 | Kosmowski et al. | 358/101 |
| 4,389,669 | 6/1983 | Epstein et al. | 358/101 |

*Primary Examiner*—Russell E. Adams
*Attorney, Agent, or Firm*—Poms, Smith, Lande & Rose

[57] ABSTRACT

A high speed optical inspection system for determining the conformity of a sample printed circuit pattern with a master circuit pattern by digitized template matching techniques including illuminating the sample pattern by high intensity lamps and filtering the incident light and reflected light, such as by cross polarization of such light, for contrasting. The contrasted pattern is viewed by an electronic video camera including a charge coupled multi-element pixel array which senses reflected points of light on the illuminated sample pattern for sending electrical signals to a micro-engine for forming a digitized image of the sample pattern. The digitized image is compared with a digitized image of the master pattern in which the digitized image of the master pattern includes an inner digitized pattern template and an outer digitized pattern template which define the inner and outer tolerances to be applied to the sample circuit pattern to determine acceptable or non-acceptable conformity of the sample pattern with the master pattern. The location of nonconforming portions of the sample pattern are identified and displayed and enlarged for inspection.

20 Claims, 10 Drawing Figures

TEMPLATE DIAGRAM FOR INNER TOLERANCE = 1
OUTER TOLERANCE = 2

Fig. 4

DEFLECTIVE IMAGE WITH ABOVE TEMPLATES

Fig. 5

HIGH SPEED OPTICAL INSPECTION SYSTEM

BACKGROUND OF THE INVENTION

Inspection and reliable verification of printed circuit patterns has been a significant cost factor in the production and manufacture of electronic systems. Such printed circuit patterns contain complex circuit configurations which may be linear or curvi-linear and in which the circuit lines, and the spaces between conductors may be quite small, as in the order of a few mils.

Human visual inspection of such circuitry with required magnification assistance is slow, time consuming, fatiguing for the inspector, often inconsistent, costly, and not reliable. Usually the speed of inspection varies from 0.5 to 2.0 square inches per minute depending upon the inspector and his state of fatigue.

Prior proposed inspection methods have included optical inspection by a "windowing technique" and by a "design rule" technique. Generally in the windowing technique a pixel by pixel comparison to a stored image of the circuitry under test is made through defined rectangular "windows". These windows must be individually manually selected by the operator. The number of windows may be in the hundreds or thousands depending upon the circuitry, and the more complex the circuitry, the more windows are required. Since the "window" areas must be manually defined the time required to "teach" the system, or prepare for the inspection of a new type of circuit, is usually many hours. Such "window" systems are limited to orthogonal arrangements with no curves or diagonal circuit portions. The speed of inspection by "windowing technique" may usually be several seconds per square inch.

The "design rule" method generally involves checking that the conductor line widths meet or exceed a predefined minimum and that spacing between conductors is never less than an allowed minimum. The design rule checking system operates locally, checks only general features which are universal to all acceptable circuit patterns, and detects only flaws which violate the design rule applied. For example, the absence of certain types of conductor segments will not violate a design rule.

SUMMARY OF THE INVENTION

The present invention relates to a high speed reliable optical inspection system utilizing a template matching technique. Generally speaking, template matching compares a digitized image of the sample circuit or other part configuration being inspected to a stored template digitized image which represents a selected acceptable or ideal master circuit configuration. Such an acceptable or ideal template can be acquired from a standard part, art work, or constructed from a data base representation of desired circuitry. Typically the templates used for reference consist of stored data which represent the minimum and maximum allowed width of the conductors being inspected. The actual conductors being inspected are required to exceed everywhere the minimum width template but to never exceed the maximum width template. Accordingly, this system recognizes defects in printed circuit boards being inspected, including an absence of a conductor where it is required such as a void or open, and the presence of a conductor where it is forbidden such as excess conductor material which could cause a short circuit.

In the template matching technique a tolerance zone is established and if any edge of a conductor or conductor material extends outside of the allowed tolerance zone a defect will be declared. For example, a 5 mil deviation at the edge of a 10 mil conductor is usually cause for concern and considered a defect. However a 5 mil deviation of the edge of a large pad may be acceptable. In the case of large features subsequent processing can be used to distinguish between the two cases mentioned above by measuring the size of the circuit feature associated with the defect. Over inspection of large areas structures and wide conductor traces can thus be avoided.

Template matching is also flexible in that it allows any shape or structure in the circuit or other part configuration to be inspected. This flexibility is particularly desirable in the inspection of very high frequency circuitry where unusual shapes are commonplace.

With regard to required computer hardware, the template matching technique requires a computer memory having a relatively large capacity to store the digitized templates. The memory capacity increases with the size of the part and the resolution employed, but with the current relatively low cost for storage, this is no problem. It may also be noted that, if the substrate under inspection is a "step and repeat" circuit pattern then only one set of circuit pattern templates need be stored.

The template technique is sensitive to registration errors, which may be controlled, for example, by the careful fixturing of each part for inspection. This sensitivity allows for better control of registration which can produce significant yield improvements in multi-layer substrates. In a template inspection system it is not difficult to provide the capability to automatically report relative alignment in X,Y axes and $\theta$, or axis of rotation, which can allow for correction of misalignment or non-registration quickly. Alternatively, the system may automatically shift the stored image of the circuit board under test with respect to the master template position data, by data processing techniques, to align the circuit board image with the stored master template.

The primary object of the present invention therefore is to provide a high speed reliable optical inspection system utilizing a template matching technique which provides many advantages over the prior proposed optical inspection systems.

An object of the invention is to provide such an optical inspection or machine vision system which is effective for routine tasks, and accomplishes such tasks at a much greater speed, and promotes a tighter controlled production process with better quality.

Another object of the invention is to provide an optical inspection system which is reliable and which inspects to a defined set of tolerance requirements.

Another object of the invention is to provide an optical inspection system for printed circuitry which enhances productivity in on-line production and also when used in off-line conditions.

More particular specific objects of the invention include the use of filters such as polarization filter to contrast the sample circuitry configuration against background areas, to obtain an accurate complete digitized image of the sample circuit configuration, and the use of light sources placed at selected high and low angles relative to the plane of the sample circuit configuration being inspected to enhance the optical imaging of the circuitry.

Another specific object of the invention is to provide a dedicated microprocessor or computer which has high speed characteristics and which may control the video camera imaging the sample circuitry, the scanning machanisms for rapidly obtaining information of the entire circuitry, and for providing the image processing, storage and analysis of the template matching technique. The invention contemplates a very high speed microcoded processor based on bipolar bit-sliced technology and in which the algorithms stored in the microprocessor provide essentially all of the data processing and data reduction associated with the actual inspection process.

A further specific object of the invention is to provide an optical inspection system, using a template matching technique in which automatic registration between the digitized image of the master circuit configuration and the digitized image of the sample circuitry configuration is readily provided, while at the same time manual registration by the operator may be utilized for adjustments of the digitized matching images to a limited degree.

A still further specific object of the invention is to provide a display showing the entire sample circuitry configuration being tested with defects in such circuitry indicated and localized and wherein the localized defects may be readily enlarged for more precise inspection.

Another specific object of the present invention is to provide an optical inspection system utilizing template matching technique wherein template tolerances are provided for inspection both inwardly of an edge of a circuit component and also outwardly of said edge to facilitate determination of acceptability or rejectability of the sample circuit. The invention contemplates that the inspector operator may control such in and out tolerances and certain other parameters during such inspection.

Another further specific object of the invention is to provide an optical inspection system having flexibility to provide adjustment of the matching images along both X and Y axes and along an axis of rotation in order to facilitate rapid comparison.

Still another specific object of the invention is to provide a color representation of the image display of defects and circuit features to facilitate the inspection process.

Other objects, features and advantages of the present invention will be readily apparent from the following detailed description and from the drawings in which exemplary embodiments of this invention are shown.

DETAILED DESCRIPTION

Figure 5:
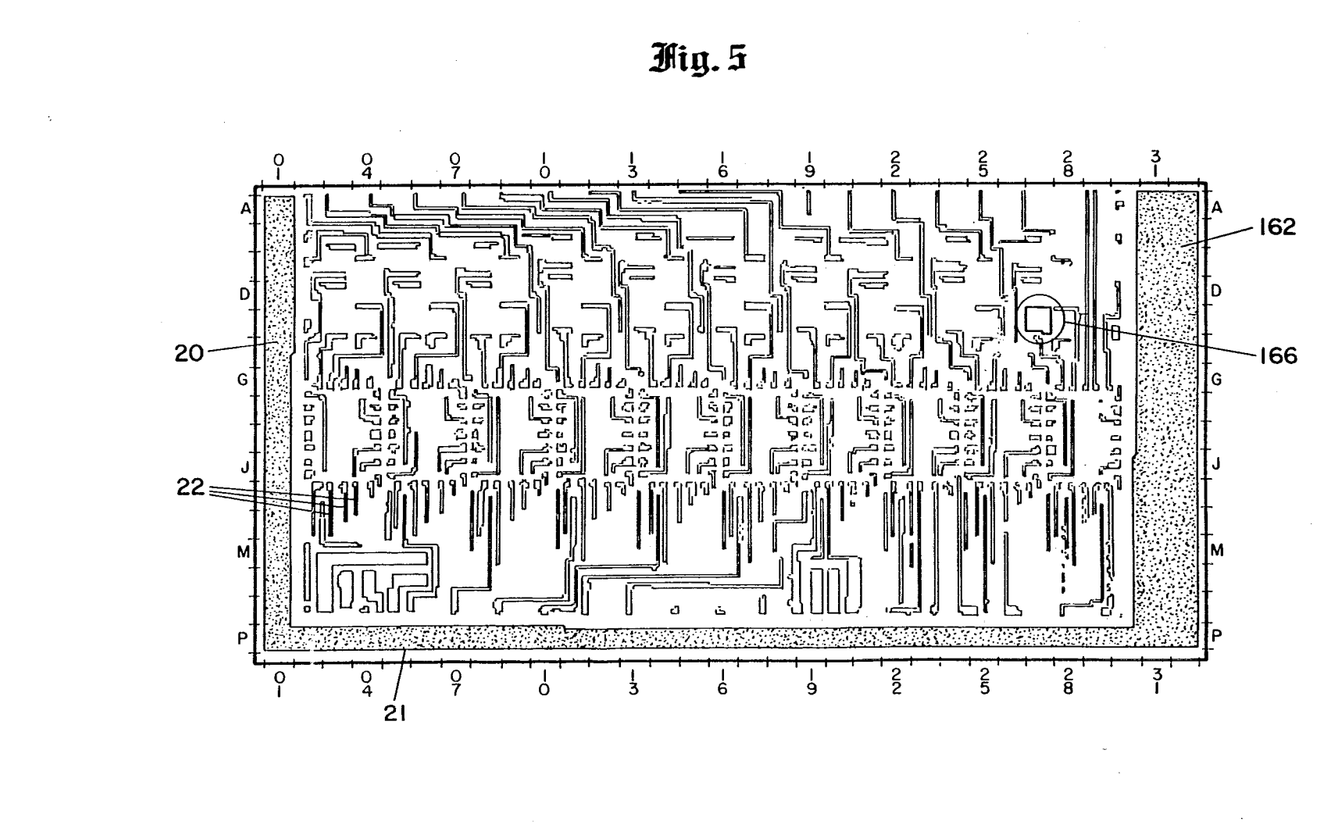
FIG. 5 is a plan view of an exemplary magnified circuit showing a defective region located at coordinates E-27.

In FIG. 5 an exemplary enlarged digitized printed circuit diagram 20 on a ceramic substrate 21 is shown. The actual physical dimensions of the substrate may be 2 inches by 1 inch and the width of lines shown such as line 22 may be 5 mils. Usually the lines 22 and other elements of the circuit are of metallic material and are applied to the substrate 21 by silkscreen processing.

Figure 1:
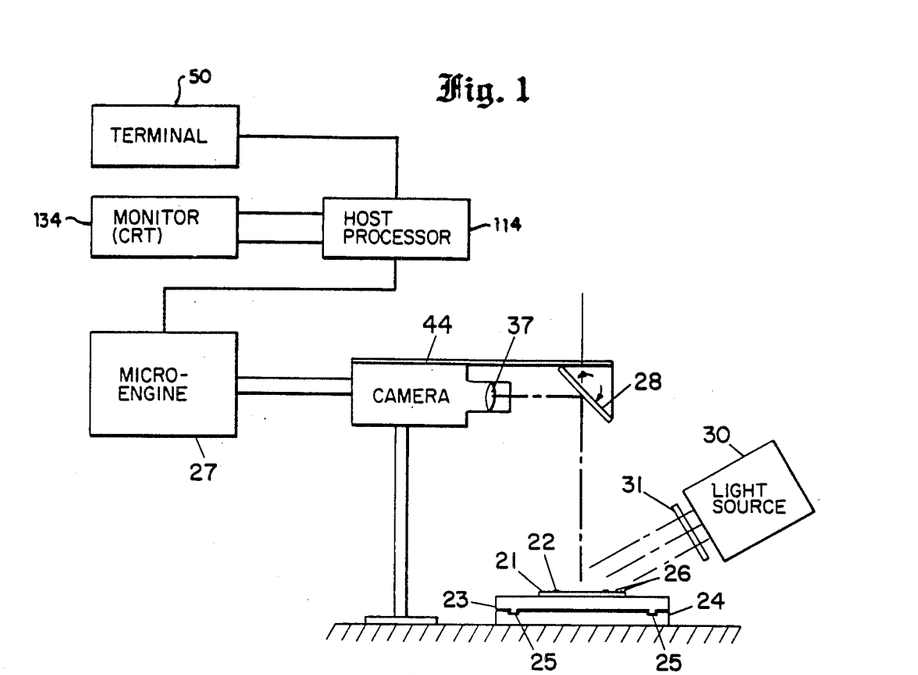
FIG. 1 is a schematic view of an optical inspection system generally embodying this invention.

In FIG. 1 substrate 21 is shown supported in a horizontal plane on a surface of a plate 23 movable on a base 24 along way means 25 along at least one axis, for example, the Y axis to facilitate scanning of the sample circuit being tested at a speed controlled by the microengine unit 27. Scanning along the X axis may be accomplished by an optical scanning mirror 28 associated with the optical system of the camera. As an alternative, scanning may be accomplished in both the X and Y directions by the optical system, with the printed circuit boards remaining stationary.

Means for registering and positioning the substrate 21 and sample configuration on plate 23 may include at least one pair of corner pins 26. Other sets of registration pins or suitable indicia on the surface of plate 23 may be used to register substrates of different dimensions. Registration of substrate 21 on plate 23 positions the sample circuit pattern relative to the optical axis of the camera, which is fixedly mounted to the base 24.

Means for illuminating the sample circuit pattern to obtain a high resolution of the edge configuration of each of the conductor lines or conductor elements on the substrate 21 may generally comprise a light source 30, FIG. 1, such as a tungsten halogen lamp of relatively high wattage such as 300 to 600 watts to provide high intensity illumination of the sample pattern and substrate. In FIG. 1 a contrasting filter means 31 may be provided to modify the incident light falling on the sample pattern and surrounding substrate surface areas. The type of filter 31 used depends upon the character of the material of the sample circuit and the material of the substrate in order to provide a maximum contrast of the circuit pattern.

As shown in FIG. 1 are the "micro-engine" unit 27, the host computer or processor 114, a color monitor or CRT 134, and an input keyboard or terminal 50.

Figure 2:
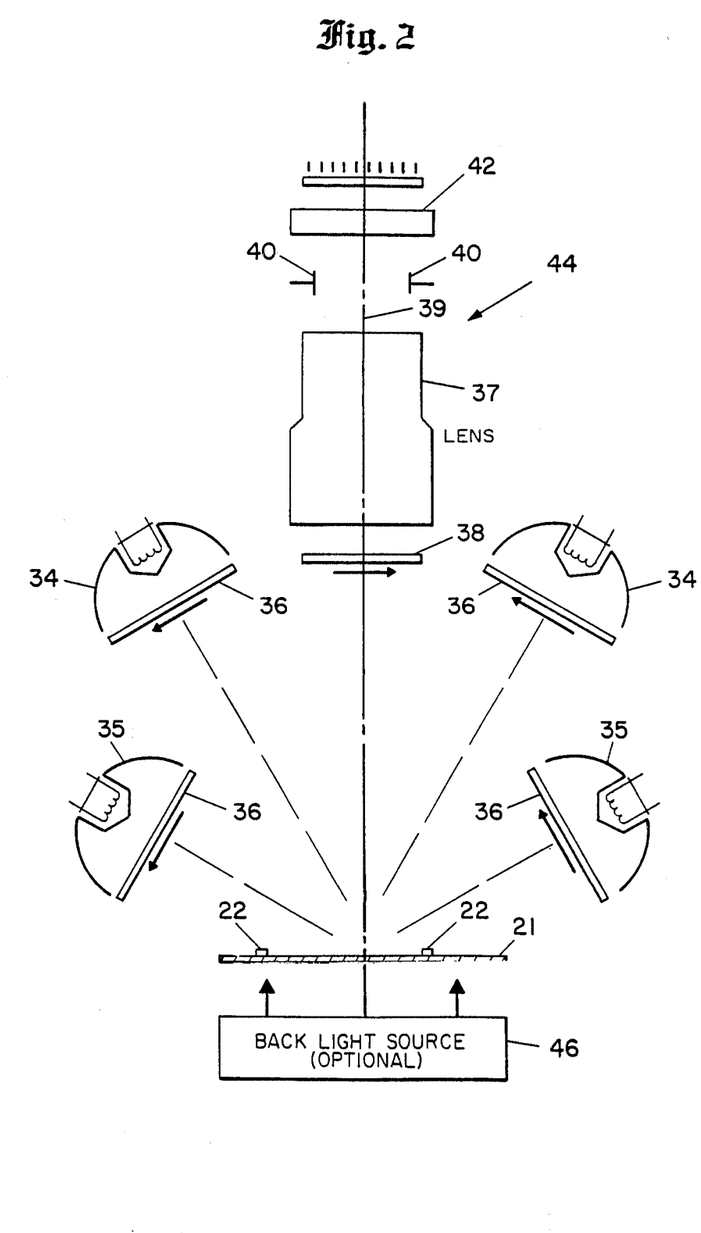
FIG. 2 is an enlarged schematic view of a modification of the means for illuminating a printed circuit pattern on a substrate being inspected in the system generally shown in FIG. 1.

In FIG. 2 a preferred method for illuminating a sample circuit pattern and substrate is shown. In FIG. 2 the substrate 21 is illuminated by two sets of lamps, each set comprising a lamp 34 and 35. Lamps 34 of each set direct their light beams at a relatively high angle with respect to the plane of the sample pattern such as in the order of 60 to 80 degrees. Lamp 35 of each set is positioned to direct its light beams toward the sample pattern at a lower angle such as about 45 degrees. To provide optimum contrast of the sample circuit elements with the material of the substrate, each of lamps 34 and 35 is provided with a polarizing filter 36 adjusted to polarize the incident light from each lamp in the same direction as indicated by arrows. The polarized incident light which is reflected from the sample metallic circuit pattern tends to preserve the polarized light and is received by the camera lens 37 through a polarizing filter 38 which is oriented perpendicular to the filters associated with the lamps so that it only transmits cross polarized light to the camera lens. The conductor image viewed by the lens as a result of cross polarization of the light received, is quite dark. Light reflected from the adjacent ceramic material of the substrate which does not tend to preserve the polarization of the light appears as a very light surface. Thus, optimum contrast between the metallic conductor elements of the sample circuit pattern and the surrounding adjacent areas of the substrate material is achieved, with the edges of the conductor elements being very precisely defined.

As shown in FIG. 2 the cross polarized light reflected from the sample pattern is transmitted along optical axis 39 through suitable light baffles 40 which inhibit stray light from entering the light path. An infrared absorption filter 42 may be positioned in said light path to further modify the light which is received by a high resolution video camera including having a charge coupled device with a 2,048 element array. Each element of the array senses the brightness of the sample pattern image at one point or pixel. The accuracy of the brightness measurement at each pixel affects the accuracy of a digital representation of the image of the sample pattern and control of illumination of the sample pattern is very important. The pixel array of the camera provides the necessary electrical input to the dedicated micro-engine 27.

In some instances the substrate material may be translucent or transparent. In such cases the printed circuit configuration may be illuminated in a contrasting manner by the use of a light source 46 positioned beneath the substrate as shown in FIG. 2. Scanning of the backlighted sample pattern is provided by scanning optical means provided between the substrate and the camera similar to the use of the scanning mirror described above.

Figure 3:
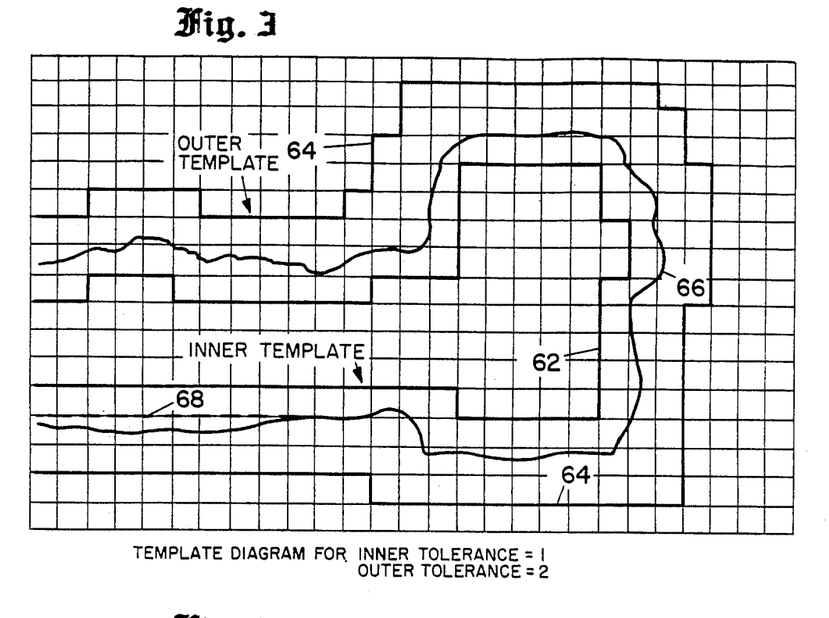
FIG. 3 is an enlarged view of a fragment of a master circuit pattern template showing an acceptable circuit pattern falling within the inner and outer tolerances.

In practice, the system of the present invention initially utilizes substantially a perfect or master circuit board and develops inner and outer templates relating to this master circuit board. Thus, for example, where FIG. 3 represents the surface of a printed circuit board, the inner template is designated by the reference numeral 62; and the outer template is designated by the reference numeral 64. The actual area covered by conductive material is the central area having a border designated 66. It may be noted that the outer edge of the deposited metallic area 66 falls between the boundaries defined by the inner template 62 and the outer template 64. Accordingly, a pattern such as that shown at 66 in FIG. 3 would indicate a satisfactory or non-defective printed circuit pattern.

Incidentally, the templates 62 and 64 are formed of a series of pixel areas, each of which may be represented by one of the squares in FIG. 3. Referring now to the dashed line 68, in FIG. 3, this is the border of the printed circuit area, for a perfect specimen. However, the inner tolerance 62 is spaced inwardly by one pixel, or one square in FIG. 3, while the outer template 64 is spaced out by two pixels from the perfect or optimum location indicated by the dashed line 68.

In practice, and as will be discussed in greater detail hereinbelow, a substantially perfect printed circuit board or master printed circuit board is initially scanned by the system, and the coordinates of an inner template such as template 62 and an outer template such as template 64 is developed and stored in a random access memory. The inner and outer templates are developed from the master circuit board by the use of preset tolerances equal to a number of pixel elements. Thus, for FIG. 3 the inner tolerance or template 62 is set at one pixel, or one square in the geometry of FIG. 3 within the line 68, while the outer template is set at 2 pixels or squares, outside of the line 68. The exact logic for developing the templates will be developed below.

Figure 4:
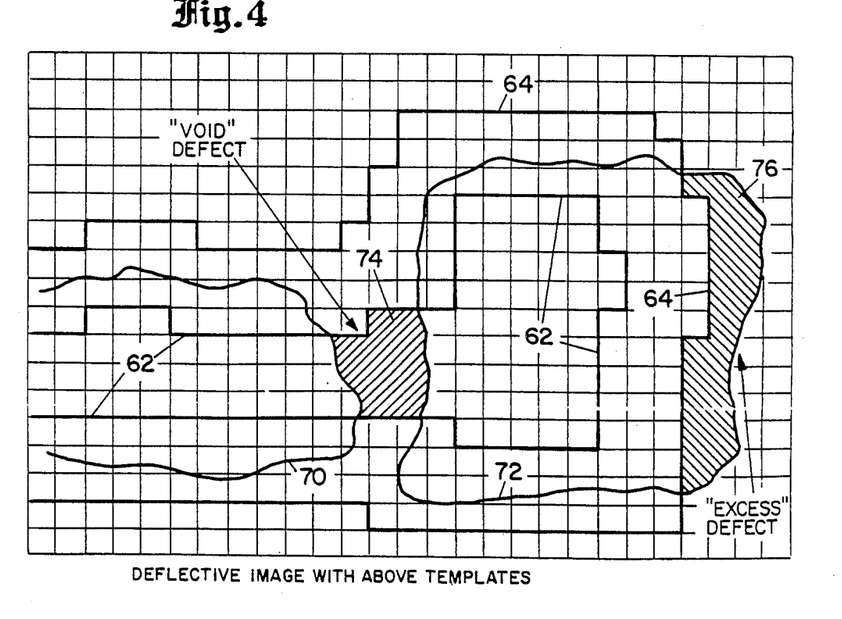
FIG. 4 is a view similar to FIG. 3 indicating two types of defects in a sample circuit pattern being matched with the master pattern of FIG. 3.

Referring to FIG. 4, a deposited layer 70, 72 is being examined to determine if its outer periphery falls within the inner and outer templates 62 and 64. In this case, there is a void as indicated by the region 74 where there is no conductive layer, so that there is a break in the circuit; and by the excess area 76 where the printed circuit material 72 extends beyond the outer template 64. Of course, when this latter type of defect occurs, there is danger that there could be a short circuit by the area 76 with an adjacent circuit area. Accordingly, the circuit of FIG. 4 includes significant defects and the board in all probability cannot be used. This is in contrast to the circuit of FIG. 3 which has its outer periphery outside of the inner template 62 and inside of the outer template 64, and is therefore within acceptable tolerances.

Figure 6:
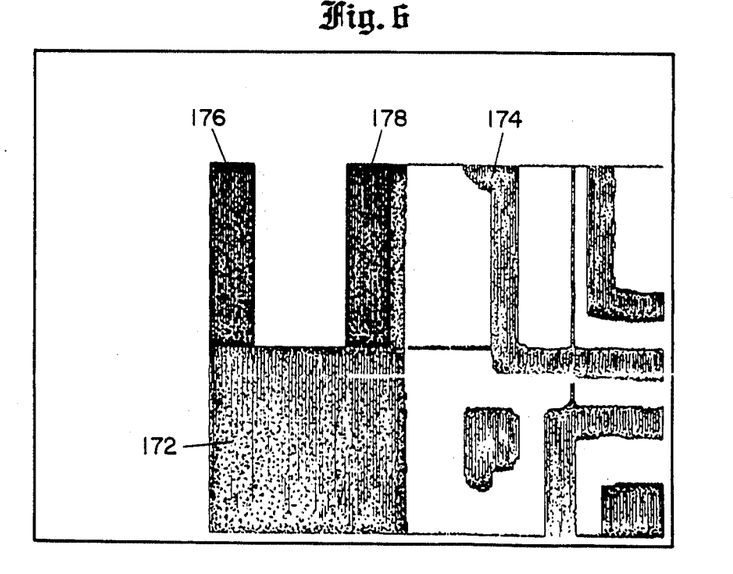
FIG. 6 is a plan view of an enlarged area of the circuit shown in FIG. 5 at coordinates A-1 and B-1.

FIGS. 5 and 6 show a printed circuit board with certain defect areas highlighted and we will return to a more complete description of FIGS. 5 and 6 hereinbelow.

Figure 7:
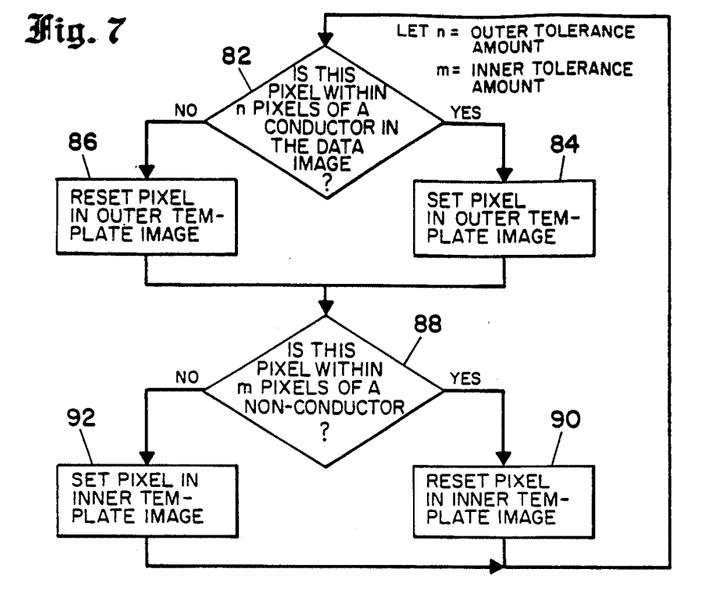
FIG. 7 is a logic diagram showing how the templates may be entered into the system memory from a master or perfect circuit board.

FIG. 7 is a logic diagram for the "learn" process. More particularly, in FIG. 7, it is assumed that a master printed circuit board is being examined. For each pixel area, a determination is made as to whether it forms part of the inner template, the outer template, or whether the pixel area is outside of both template areas. For the purposes of FIG. 7, it is assumed that the letter "n" represents the outer tolerance amount of pixels, which was 2 in FIGS. 3 and 4; and m=the inner tolerance amount in pixels, which was equal to 1, in the example of FIGS. 3 and 4. The first question asked by the logic diamond 82 in FIG. 7 is "Is this pixel within n pixels of a conductor in the data image?" If the answer is "yes," then, in the random access memory location, corresponding to the particular pixel being examined, the memory element is set to a predetermined "set" state, as indicated by the block 84. However, if the answer to the inquiry posed by block 82 is "no", then the pixel in question is reset to the other state, as indicated by the block 86 in FIG. 7.

In the lower part of the logic diagram of FIG. 7, the inner template is defined, initially by the question asked in block 88, "Is this pixel within m pixels of a non-conductor?" If the answer is "yes", then the particular pixel should not be within the inner template and the pixel memory designation is reset, as indicated by block 90. However, if the pixel is not within m pixels of a nonconductor, then the memory location corresponding to that pixel in the inner template memory is "set" as indicated by the block 92. The result is that two template images are stored in the dedicated computer circuitry or micro-engine, both of which resemble the master printed circuit pattern, but with one being slightly enlarged as to the width of the conductors and conducting areas, and the other being slightly reduced.

Figure 8:
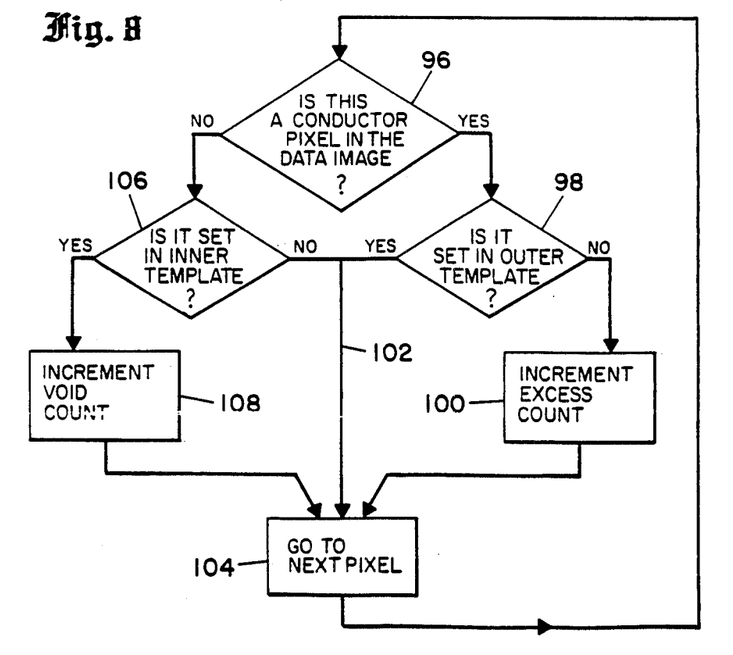
FIG. 8 is a diagram for the inspection logic which is employed in an illustrative embodiment of the invention.

The logic diagram of FIG. 8 involves the inspection process of the type shown in FIG. 4, where a new untested printed circuit board is placed in the unit and tested against the inner and outer templates previously developed from a master circuit board. More particularly, as shown in FIG. 8, the first question indicated by the diamond 96 is, "Is this a conductor pixel in the data image?" Thus, with the preferred embodiment as described hereinabove, the camera would be looking at and seeing a dark area of the image, and this would represent an area where the conductor material is present. If the answer is "yes", then we proceed to the next question as indicated in diamond 98, "Is it set in the outer template?" If the answer is "no", this would corespond to a pixel in the area 76 in FIG. 4 indicating that the conductor has exceeded the outer template area, and accordingly, as indicated by block 100, a counter which records excess increments of conductor is pulsed to increase the count recorded relative to this type of defect.

If the answer to the question of diamond 98 is "yes", then the conductive area is within the outer template, as it should be, and the line 102 leading to the block 104 indicates that the system is incremented to the next pixel for a repeat of the cycle shown in the logic diagram of FIG. 8.

Returning to a "no" answer for the question of diamond 96, this means that we are looking at an insulating area, and we proceed to the question of diamond 106, "Is it set in the inner template?" A "no" answer indicates that the insulating area is not within the inner template, and accordingly, there is no defect and we return to block 104 to step to the next pixel. However, a "yes" answer to the question of diamond 106 indicates that we have an insulating area within the inner template 62 where there should be a conductive area, such as the defect shown at 74 in FIG. 4. Block 108 indicates that the counter for determining the number of void pixels is incremented when this type of defect is encountered. Incidentally, as may be seen from the number of squares within the areas 74 and 76, the counts may reach fairly large numbers rapidly, if there are any substantial missing areas from the desired printed circuit path, or if there are any extended excess areas of the type shown at 76.

Figure 9:
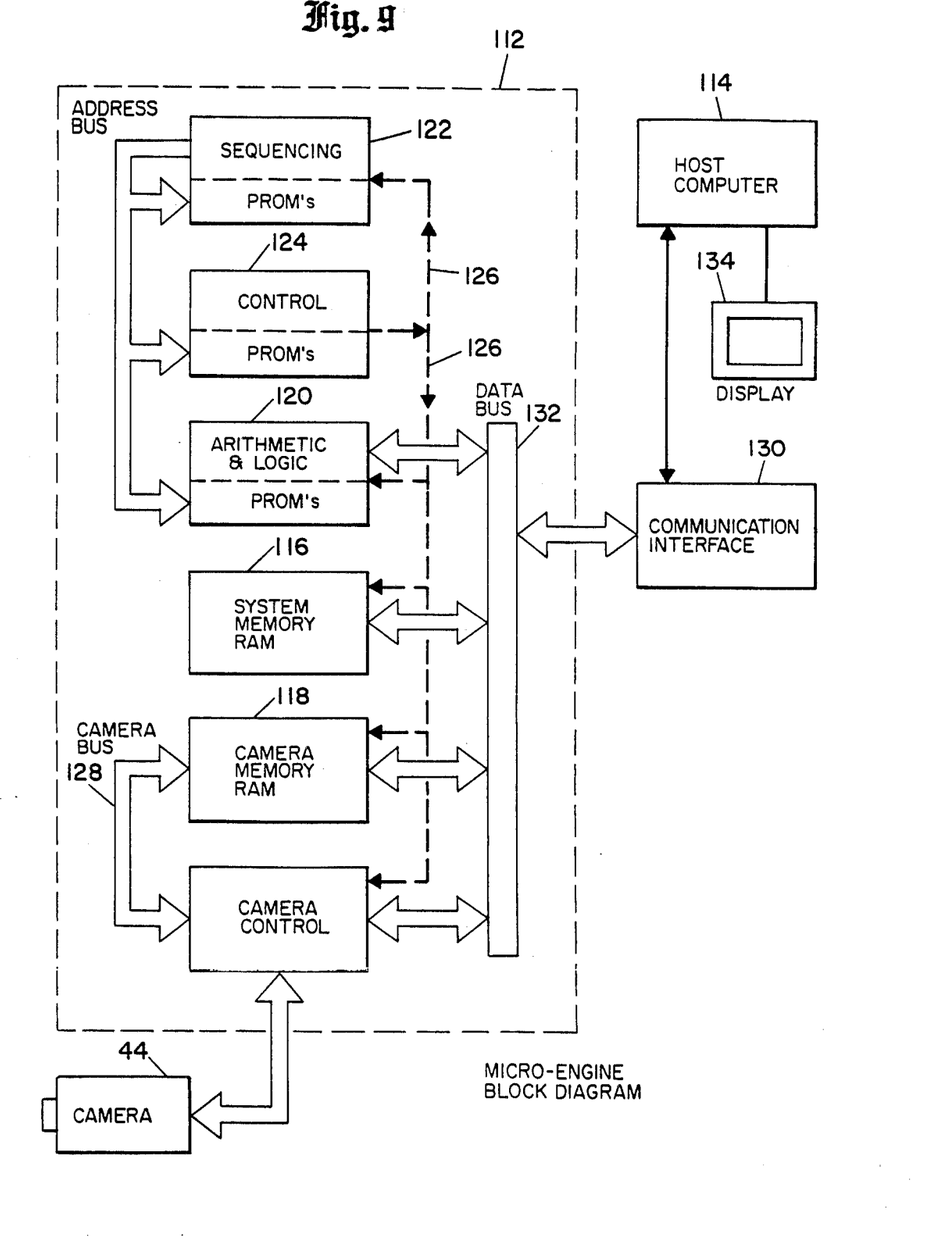
FIG. 9 is a block circuit diagram showing the dedicated "micro-engine" and the associated host computers and camera, illustrating the principles of the invention.

FIG. 9 is a block circuit diagram setting forth the interrelationship between the micro engine 112 included within the dashed line block 112, (referred to as 27 in FIG. 1), the camera 44, and the host computer 114. Included within the micro-engine 112 is the system memory 116 within which the templates are stored in terms of "set" or "reset" conditions for each pixel included in the printed circuit board areas being scanned. The system memory is a relatively large random access memory which may include from one to 20 megabytes of information. The camera memory 118 stores the information relative to each pixel of a scanned printed circuit board to be inspected and indicates whether each pixel area is conductive or non-conductive. Logic functions of the type indicated in FIGS. 7 and 8 of the drawings are accomplished by the arithmetic and logic unit 120 together with the programmable read-only memories (PROMS) which are included in this unit. The overall sequencing of the mode of operation of the unit is controlled by the sequencing unit 122 which includes the programmable readonly memory units which establish the sequence of steps to be taken. Control and the transfer of information between the circuits of the micro-engine 112 is accomplished by the control unit 124 which also includes PROMS. It may be noted that the dashed line circuits 126 leading from the control unit 124 to the other components of the micro-engine serve to coordinate the transfer and flow of information between these components. The camera bus 128 facilitates the coordination of information relative to the position of the mirror associated with the camera identifying a particular pixel, along with the position information from the printed circuit board supporting member, with the storage of information within the camera memory 118. The micro-engine 112 communicates with the host computer 114 through the communication interface 130 and the data bus 132. The display unit 134 may be a color cathode ray tube or video display upon which the printed circuit board may appear, with particular color indications showing the areas having defects. Through the use of a local specialized micro-engine 112, rather than using a general purpose computer, very high speed action may be accomplished. Thus, many thousands of pixels on a small two inch by two inch circuit board may be scanned and the board inspected in less than a second.

Figure 10:
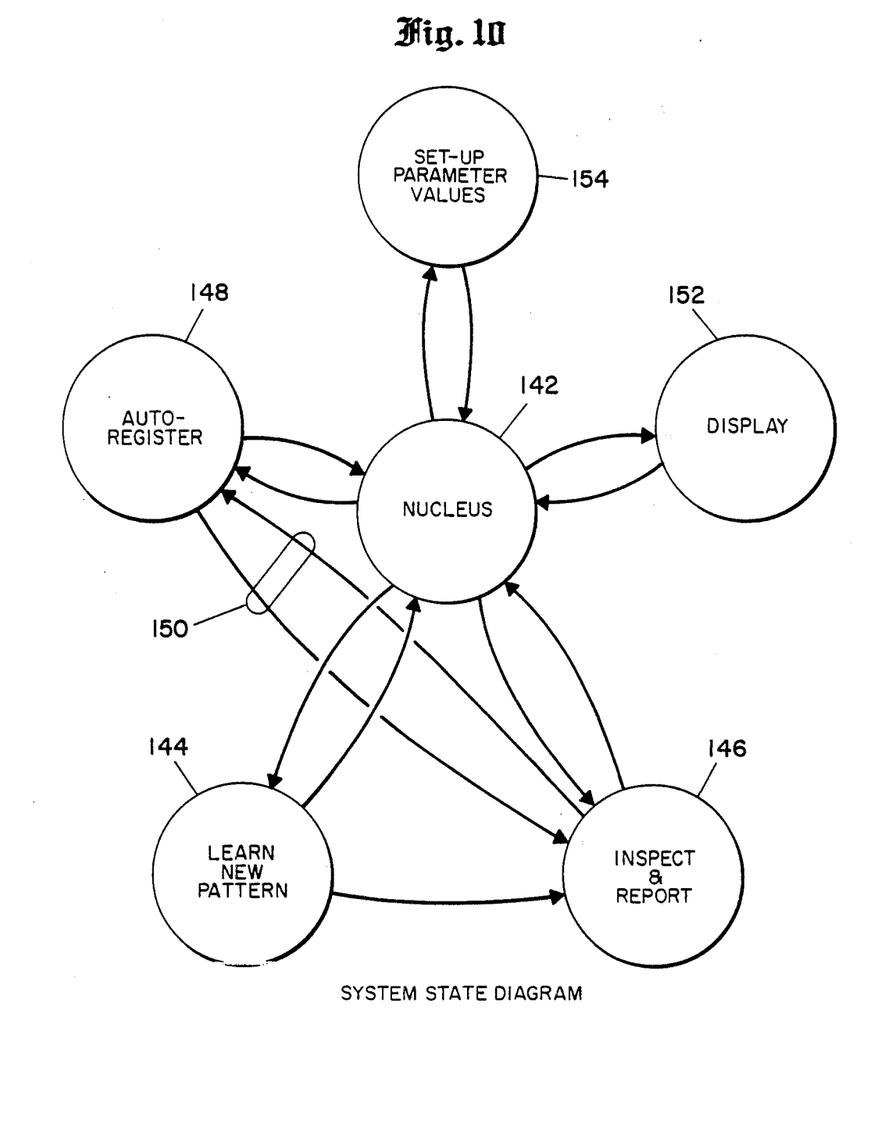
FIG. 10 is a system state diagram indicating the mode of operation of the system of FIG. 9.

FIG. 10 is a software state diagram of the system of the present invention. More specifically, the central area 142 entitled "nucleus" represents the waiting mode of the system. When an instruction from the host computer to "learn" is received, the computer system shifts into the mode 144 designated "learn new pattern" in FIG. 10. After the new pattern has been "learned", and the two templates stored in the system memory 116 (see FIG. 9) then the system is prepared to shift directly into the "inspect and report" mode 146, when a new board to be inspected is placed on the platform, and an appropriate signal is given by a foot pedal or the like.

The auto register mode 148 is shown directly linked to the "inspect and report" mode 146 by the arrows 150. Thus, if an unusually large number of initial errors appear on the display 152, it may be the result of a slight misalignment or non-registration of the position of the new printed circuit board being inspected as compared with the template data stored in the system memory 116. The auto register mode 148 shifts images in the memory 118 to obtain a better "fit" and permit a re-inspection with fewer or no errors.

The remaining mode 154 involves "set-up parameter values", and this would involve initial establishment of factors such as (1) scan rate, (2) brightness of illumination, (3) the size of the printed circuit board to be learned and to be inspected, (4) the tolerances for the inner and outer templates as discussed hereinabove in connection with FIG. 3, and the like.

Now, returning to FIG. 5, this figure represents a display which will appear on the display unit 134 associated with the host computer 114. Although the printed circuits do not appear as prominently as would be desirable, the printed circuit areas are those which are shaded, as indicated at reference numerals 20, 22 and 162, whereas the bare circuit board is represented by the white areas as shown at 21, for example. The legend which appears immediately below the printed circuit board is "one defective region", and in the display 134, the circuit board would appear as shown in FIG. 5 with the associated legends. The display is preferably colored and the single defective region would be marked by a special color as indicated by the generally rectangular area within the circle 166 as shown in FIG. 5. It may also be noted that, along the edges of the circuit board appear letters in the vertical direction and numbers in the horizontal direction. Further, the defect coordinates are identified as "E-27" to indicate the vertical and horizontal position of the defect, in accordance with the letters and numbers along the edges of the substrate.

The system is also set up to provide an enlarged view of any selected portion of the circuit board under test, by punching in the coordinates such as "E-27" in connection with FIG. 5, or the area "A-1" as shown in FIG. 6. In FIG. 6, the upper left-hand corner designated "A-1" is shown to a greatly enlarged scale. However, the particular board shown in FIG. 6 had a missing conductive area in the "A-1" area. Thus, the regular printed circuit areas are shown in moderately light shading as indicated at reference numeral 172 and 174, for example. The area bounded by the two dark rectangles 176 and 178 was supposed to be plated with a layer of conductive material, but it was missing from the sample shown in FIG. 6. Accordingly, the display 134 showed first that there was a defect in region "A-1", and then, upon command, provided the blown-up view of FIG. 6, with the areas 176 and 178 marked in bright red.

For completeness, certain additional information will now be provided. The host computer 114 may, for example, be a Z-80 CPU, with 64 kilobytes of random access memory, and may be purchased from the well-known supplier of digital circuits, Jonos. The host computer also includes floppy disk drives, a graphics controller, and a keyboard terminal (50 in FIG. 1) for operator interface. The floppy disk drives may be provided by Sony, and the graphics controller may be one made by Matrox.

In connection with FIGS. 3 and 4, a preferred system has been described in which inner and outer templates are stored and observed points are compared with both of these templates. Alternatively, a single precise template could be stored, and calculations could be performed with regard to each pixel on each board being inspected, to determine whether each pixel of a board being inspected is (1) conductive or nonconductive; and then (2) pixel proximity tolerances for each conductive or non-conductive pixel would be calculated. However, it is normally quicker to use the tolerance calculations only once, to provide the digitized inner and outer master templates;and then only a simpler pixel-by-pixel comparison with the two templates need be made in the course of inspection each of the many corresponding boards to be inspected.

In conclusion, it is to be understood that the system as shown in the drawings and described is illustrative of the principles of the invention; and various alternatives may be made. Thus, by way of example and not of limitation, the lights and camera may be provided with colored filters, either band pass or band stop filtering, to assist in distinguishing between the conductive and non-conductive areas; and the logical arrangement of the computer system may be varied from the precise form shown in FIG. 9. Accordingly, it is to be understood that the system is not limited to that precisely as described hereinabove and shown in the drawings.

I claim:

1. A method of high speed optical inspection of a sample configuration by comparing the sample configuration with a digitized image of a selected master configuration, comprising the steps of:
    providing in a digital memory the digitized representation of said master configuration,;
    selecting an outer set of digitized tolerances representing an outer defect limit for the master configuration; incrementing the digitized representation of the master configuration to the outer set of digitized tolerances to provide an outer digitized template;
    selecting an inner set of digitized tolerances representing an inner defect limit for the master configuration;
    incrementing the digitized representation of the master configuration to the inner set of digitized tolerances to provide an inner digitized template;
    positioning the sample configuration to be inspected on a support surface;
    positioning a video camera to obtain an image of the sample configuration;
    illuminating the sample configuration by a light source to contrast said sample configuration against a background;
    scanning said illuminated sample configuration to obtain digitized signals representing successive areas of the sample configuration;
    comparing the digitized signals from the sample configuration with the inner and outer templates; and
    indicating conformity or nonconformity of the sample configuration with the master configuration as defined by the outer and inner template representations.

2. The method of claim 1 wherein the master configuration is a pattern of conductors on a circuit board, and wherein the step of providing the digitized representation of the master configuration includes:
    positioning a master or substantially perfect circuit board having the master configuration thereon on a support surface;
    positioning the video camera to obtain an image of the master configuration;
    illuminating the master configuration by the light source means directing light at an angle toward the master configuration to contrast the master configuration against adjacent substrate areas;
    scanning the illuminated master configuration to obtain a video image of the entire master circuit configuration; and
    digitizing the scanned master image.

3. The method of claim 1 further including the step of:
    storing in memory the digitized representation of the master configuration.

4. The method of claim 3 wherein the sample positioning step includes the step of:
    selectively displacing the digitized image of the sample configuration with respect to the digitized image of the master configuration along X and Y axes and about an axis of rotation to position the digitized images in registration with one another.

5. The method of claim 1 wherein the sample positioning step includes the step of:
    positioning the sample along X and Y axes and about an axis of rotation to assure registration of the digitized image of the sample configuration with the stored digitized image of the master configuration.

6. An apparatus for high speed inspection of sample patterns such as patterns having linear and/or curvilinear configurations, comprising:
- means for providing digitized representations of a master pattern, said representations including inner and outer templates derived from said master pattern representing permissible inner and outer sets of tolerances for said master pattern;
- means for illuminating said sample pattern to contrast said sample pattern against a background;
- means for scanning said illuminated sample pattern;
- means for obtaining and digitizing signals from the scanning of said illuminated sample pattern;
- means for comparing the digitized signals from the sample pattern with the digitized inner and outer templates derived from the master pattern; and
- means for indicating portions of the sample pattern which are within the inner template and/or without the outer template.

7. The apparatus of claim 6, wherein the means for providing digitized representations of the master pattern comprises:
- means for scanning a circuit board having the master pattern thereon;
- means for digitizing the scanned master pattern;
- means for storing the digital representation of the master configuration;
- means for deriving and storing an inner digital template representing the digitized master configuration incremented by a preselected inner defect limit;
- means for deriving and storing an outer digital template representing the digitized master configuration incremented by a preselected outer defect limit.

8. The apparatus of claim 6 wherein the means for scanning the sample configuration includes:
- means for positioning a sample configuration to be inspected on a support surface;
- means for moving a video camera relative to the sample configuration to provide a video image of the entire sample configuration;
- means for digitizing the video image for comparison with the inner and outer templates.

9. The apparatus of claim 6 further comprising:
- means for indicating portions of the sample configurations which fall within the inner template and/or without the outer template.

10. The apparatus of claim 9, wherein the means for indicating nonconforming portions of the sample pattern includes:
- means for displaying the location and character of the nonconforming portions of the sample pattern being inspected.

11. The apparatus of claim 6 further including means for shifting the registration position of the digitized sample configuration relative to the digitized master configuration.

12. The apparatus of claim 6 further including:
- means for shifting the relative positions of the master and sample configurations along X and Y axes and about an axis of rotation to assure registration of the configurations with one another.

13. A method of automatic electro-optical inspection of a sample object by comparing an electronic image of said object with the electronic image of a selected reference object, comprising the steps of:
- providing an electronic representation of said reference object, including electronic representations of inner and outer templates derived from said reference object representing permissible inner and outer sets of tolerances in the configuration of said reference object;
- scanning said sample object to obtain an electronic image thereof;
- comparing the electronic image of the sample object with the electronic representations of said inner and outer templates; and
- indicating conformity or nonconformity of the sample object with the reference object as defined by the outer and inner templates.

14. The method of claim 13 further including the step of:
- identifying and locating nonconforming portions of the sample circuit configuration.

15. The method of claim 14 further including the step of:
- displaying nonconforming portions of the sample circuit configurations.

16. The method of claim 15 further including the step of:
- enlarging the displayed nonconforming portions of the sample circuit configuration.

17. The method of claim 16 further including the step of:
- displaying enlarged nonconforming portions of the sample circuit configuration in color to identify character of the nonconforming circuit portions.

18. The method of claim 13, wherein the reference object electronic representation providing step includes:
- scanning the selected reference object to obtain an electronic image thereof and storing in electronic memory the electronic image thereof; and wherein the method further includes the step of:
- selectively displacing the electronic image of the sample configuration with respect to the electronic image of the master configuration along X and Y axes and about an axis of rotation to position the electronic images in registration with one another.

19. The method of claim 13, further comprising the step of:
- positioning the sample along X and Y axes and about an axis of rotation to assure registration of the electronic image of the sample configuration with the electronic image of the master configuration.

20. A method of automatic electro-optical inspection of a sample object by comparing an electronic image of said object with the electronic image of a selected reference object, comprising the steps of:
- providing an electronic representation of said reference object, including electronic representations of inner and outer templates derived from said reference object representing permissible inner and outer sets of tolerances in the configuration of said reference object;
- scanning the selected reference object to obtain an electronic image thereof;
- storing in electronic memory the electronic image of the reference object;
- scanning said sample object to obtain an electronic image thereof;
- selectively displacing the electronic image of the sample configuration with respect to the electronic image of the master configuration along X and Y axes and about an axis of rotation to position the electronic images in registration with one another;

comparing the electronic image of the sample object with the stored electronic representations of said inner and outer templates; and indicating conformity or nonconformity of the sample object with the reference object as defined by the outer and inner templates.

* * * * *